(12) United States Patent
Dane et al.

(10) Patent No.: US 9,149,336 B2
(45) Date of Patent: Oct. 6, 2015

(54) SYSTEM AND METHOD FOR PROVIDING A METAL STERILIZATION TRAY

(75) Inventors: Gary T. Dane, Bow, NH (US); Jon D. Shoemaker, Leesburg, IN (US)

(73) Assignee: Symmetry Medical Manufacturing Inc., Warsaw, IN (US)

( * ) Notice: Subject to any disclaimer, the term of this patent is extended or adjusted under 35 U.S.C. 154(b) by 1102 days.

(21) Appl. No.: 12/828,657

(22) Filed: Jul. 1, 2010

(65) Prior Publication Data

US 2011/0002811 A1 Jan. 6, 2011

Related U.S. Application Data

(60) Provisional application No. 61/222,661, filed on Jul. 2, 2009.

(51) Int. Cl.
*A61L 2/26* (2006.01)
*A61B 19/02* (2006.01)
*A61L 2/00* (2006.01)

(52) U.S. Cl.
CPC ........... *A61B 19/026* (2013.01); *A61B 19/0271* (2013.01); *A61L 2/26* (2013.01); *A61B 2019/0213* (2013.01); *A61B 2019/0278* (2013.01); *A61L 2/00* (2013.01)

(58) Field of Classification Search
CPC ..................................... A61L 2/00; A61L 2/26
USPC .......................................................... 422/297
See application file for complete search history.

(56) References Cited

U.S. PATENT DOCUMENTS

| | | | | |
|---|---|---|---|---|
| 2,674,536 | A * | 4/1954 | Fisher | 426/114 |
| 3,494,723 | A * | 2/1970 | Gray | 422/21 |
| 5,525,314 | A * | 6/1996 | Hurson | 422/300 |

* cited by examiner

*Primary Examiner* — Lyle Alexander
(74) *Attorney, Agent, or Firm* — Hayes Soloway PC

(57) ABSTRACT

The system contains a metal tray formed from a sheet of metal. A plurality of pockets is formed in the metal tray, wherein the plurality of pockets is formed from manipulating the sheet of metal. A cover is formed over the metal tray. Optionally, a base may be engaged with the cover, wherein the metal tray is formed to fit snugly between the cover and the base.

6 Claims, 7 Drawing Sheets

SYSTEM AND METHOD FOR PROVIDING A METAL STERILIZATION TRAY

CROSS REFERENCE TO RELATED APPLICATION

This application claims benefit of U.S. Provisional Application Ser. No. 61/222,661 filed Jul. 2, 2009, the entire disclosure of which is incorporated herein by reference.

FIELD

The present disclosure is generally related to sterilization trays and, more particularly, is related to a sterilization tray formed from a metal sheet.

BACKGROUND

Sterilization trays are used in the medical profession for holding medical instruments. The sterilization trays may be inserted into an autoclave for sterilizing the medical instruments. The sterilization trays may also be used for transporting medical instruments and may be used in various medical settings, such as in an operating room, to retain and organize medical instruments for surgery or other medical application. In these settings, the sterilization trays are exposed to the same contamination hazards as the medical instruments.

Sterilization trays generally are made porously. That is, the sterilization trays are made to allow cleaning fluids, including liquids and gasses, to pass through the trays. Porosity is achieved by forming openings all about the sterilization tray. Within the autoclave, liquids and/or gasses permeate the sterilization trays to clean the medical instruments within the sterilization trays as well as the inner surfaces of the sterilization trays.

Sterilization trays generally are arranged to allow medical instruments to sit flat within the tray and keep multiple instruments from jostling against each other. In particular, sharp medical instruments, if allowed to jostle about within the sterilization trays, may bump the tray and lose some of its carefully honed edge, may bump the handles of other instruments and damage those handles, and may retain some fragment of the other handles on its blade, which may then be introduced beneath the skin of a patient. As a result, sterilization trays are frequently designed to segregate the instruments. Segregation of instruments is generally achieved by attaching brackets, dividers, or other items to the sterilization trays to hold each instrument or establish barricades between instruments.

When a bracket, divider, or other item is attached to the sterilization tray, a crevice is created between the item and the sterilization tray. The crevice may receive a contaminant while exposed to contamination hazards. Further, the crevice effectively may shield the contaminant from the fluids and/or gasses of the autoclave, impeding removal of the contaminant. As a result, construction of sterilization trays frequently involves minimizing the existence of crevices and attempting to create seals in these locations to minimize the entry of contaminants into the crevices. Seals, however, do wear down, particularly with the regular and rigorous cleaning effort of the autoclaves.

Another problem with many sterilization trays is weight. Sterilization trays are transported by nurses, primarily. With instruments, sterilization trays can weigh as much as thirty pounds. Nurses have been known to remove brackets and other interior pieces of the sterilization trays to diminish the weight of the sterilization trays, exposing the medical instruments to damage.

Thus, a heretofore unaddressed need exists in the industry to address the aforementioned deficiencies and inadequacies.

SUMMARY

Embodiments of the present disclosure provide an apparatus and method for providing a sterilization apparatus. Briefly described, in architecture, one embodiment of the system, among others, can be implemented as follows. The apparatus contains a metal tray formed from a sheet of metal. A plurality of pockets is formed in the metal tray, wherein the plurality of pockets is formed from manipulating the sheet of metal. A cover is formed over the metal tray.

The present disclosure can also be viewed as providing methods for forming a sterilization apparatus. In this regard, one embodiment of such a method, among others, can be broadly summarized by the following steps: providing a mold of a sterilization tray, the mold having a plurality of pocket-forming structures; conforming a metal sheet to the mold, thereby forming a metal tray having a plurality of pockets formed from the plurality of pocket-forming structures; removably securing a cover to the metal tray; and forming a plurality of holes through at least one of the metal tray and the cover.

The present disclosure can also be viewed as providing methods of sterilizing a medical instrument. In this regard, one embodiment of such a method, among others, can be broadly summarized by the following steps: providing a metal tray formed from a sheet of metal, the metal tray having a plurality of pockets formed within the metal tray from manipulating the sheet of metal; placing at least one medical instrument within at least one of the plurality of pockets; removably securing a cover to the metal tray; and placing the metal tray having the removably secured cover within a medical instrument sterilization environment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale. Instead emphasis is being placed upon illustrating clearly the principles of the present disclosure. Moreover, in the drawings, like reference numerals designate corresponding parts throughout the several views.

DETAILED DESCRIPTION

Figure 1:
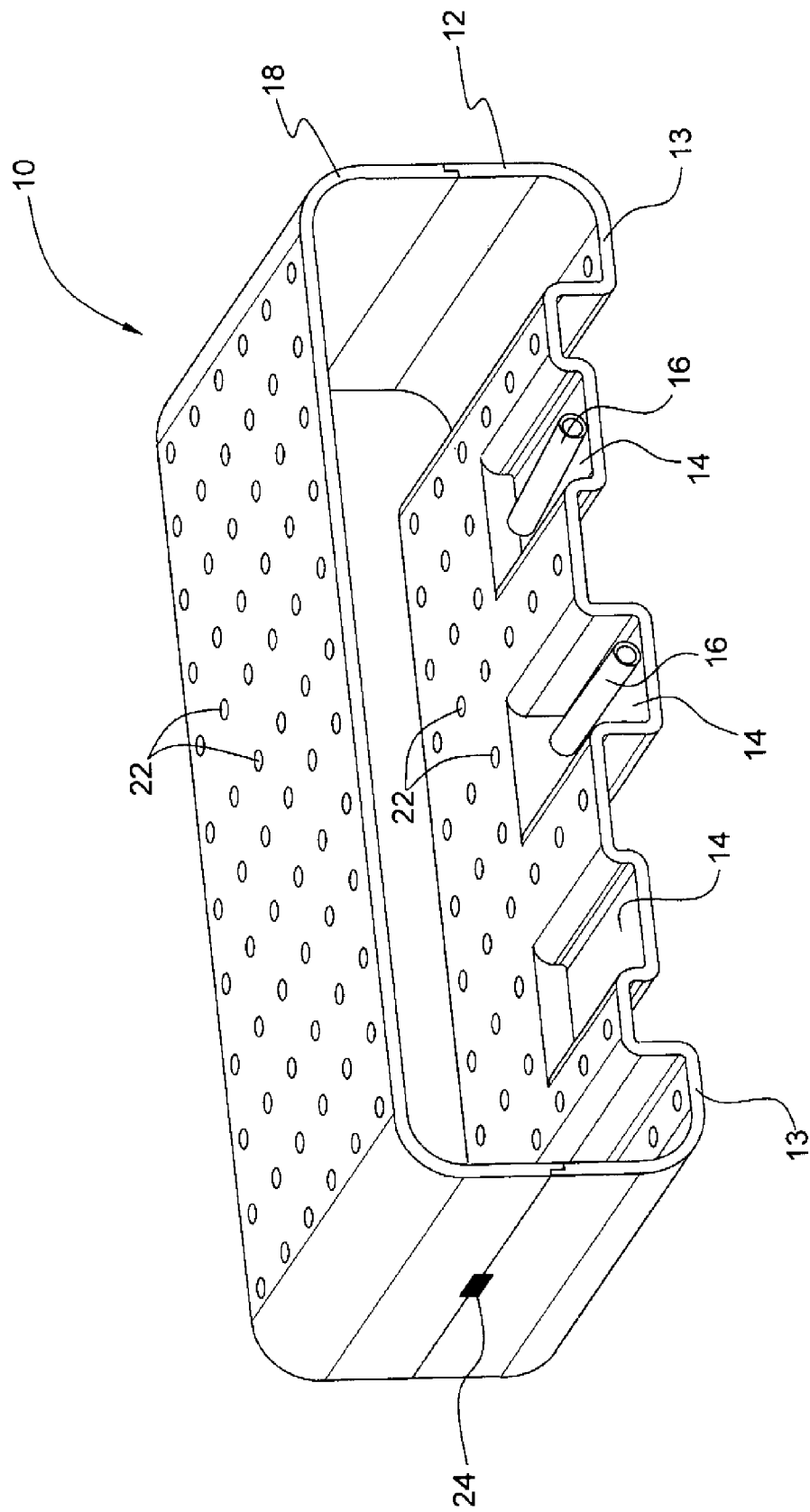
FIG. 1 is an illustration of a cross-sectional plan view of a sterilization apparatus, in accordance with a first exemplary embodiment of the present disclosure.

FIG. 1 is an illustration of a cross-sectional plan view of a sterilization apparatus 10, in accordance with a first exemplary embodiment of the present disclosure. The sterilization apparatus includes a metal tray 12 formed from a sheet of metal. A plurality of pockets 14 is formed in the metal tray 12, wherein the plurality of pockets 14 is formed from manipulating the sheet of metal. A cover 18 is formed over the metal tray 12. The A plurality of openings 22 is formed within the cover 18 and the metal tray 12. The sterilization apparatus 10 may house a quantity of medical instruments 16 within the pockets 14.

The metal tray 12 is formed from a sheet of metal through a molding or forming process. Any molding or forming process may be used to form the metal tray 12 from the sheet of metal. During the molding or forming process, the sheet of metal is manipulated to form a specific design of the metal tray 12. This design includes a metal tray 12 with at least one pocket, more commonly a plurality of pockets 14, formed from pocket-forming structures within a mold. The pockets 14 are sized to house one or more medical instruments 16 during a sterilization process. The metal tray 12 may be constructed from a variety of metals, metal compositions or metal-based materials. For example, the metal tray 12 may be constructed from stainless steel, aluminum or another sterilization-safe material.

As discussed previously, the metal tray 12 may be formed using a variety of forming and molding processes. One type of forming process is known as thermoforming, wherein metal sheets, such as aluminum sheets, are heated to a temperature fitting within a superplastic temperature window of the metal. At the superplastic temperature, the metal sheets are malleable, while maintaining sufficient integrity to avoid uneven thinning. The heated metal sheet is set to a mold and the metal sheet conforms to the mold over a period of about 10 minutes, for example. Other metallic materials may be thermoformed using a similar process with varying conditions, such as different superplastic temperature windows and different lengths of time. Using the thermoforming process, the metal tray 12 may be formed from a unitary sheet of metal that retains and segregates medical instruments without the need for additional brackets, dividers and the like. The number of crevices can be reduced or eliminated by avoiding attachment elements. Also, if aluminum or another lightweight metal is selected, the metal tray 12 may be made lighter than a comparable plastic tray due to the weight of the aluminum and the avoidance of additional parts.

Another process to form or mold the metal tray 12 is known as hydroforming. Hydroforming includes using metal sheets, such as aluminum sheets, that are pressed against a mold by an expanding bladder that increases pressure on the metal sheets as the bladder expands. Characteristics of a hydroforming process may vary depending on the metal sheet selected. Using the hydroforming process, the metal tray 12 may be formed from a unitary sheet of metal that retains and segregates medical instruments 16 without the need for additional brackets, dividers and the like. The number of crevices can be reduced or eliminated by avoiding attachment elements. Also, similar to thermoforming, if aluminum or another lightweight metal is selected, the metal tray 12 can be made lighter than a comparable plastic tray due to the weight of the aluminum and the avoidance of additional parts.

The metal tray 12 is formed with at least one pocket 14, which may include a variety of designs, depending on the intended use of the sterilization apparatus 10, the sterilization process and/or the type of medical instruments 16 used with the sterilization apparatus 10. The pockets 14 may segregate the medical instruments 16 from each other, and preferably, the pockets 14 operate to maintain the medical instruments 16 in a static position. The pockets 14 may be formed to universally fit a variety of medical instruments 16 having a variety of dimensions or the pockets 14 may be formed to fit a particular medical instrument 16 with a friction fit. In accordance with this disclosure, a pocket 14 formed to friction fit a medical instrument 16 may include any pocket 14 design that is capable of retaining a medical instrument 16 within a substantially stationary position. A pocket 14 may be formed to be significantly larger than a medical instrument 16 in all by a select few portions of the medical instrument 16. Accordingly, at these select few portions of the medical instrument 16, the pocket 14 may be positioned to snugly hold a medical instrument 16 in a substantially stationary position. A user of the sterilization apparatus 10 may insert and remove a medical instrument 16 from the friction fit pocket 14 with minimal force, wherein the portion of the pocket 14 that is snugly proximate to the medical instrument 16 is biased while the medical instrument 16 is being inserted and removed.

The pockets 14 may also include a variety of other designs to enhance the usability or the efficiency of the sterilization apparatus 10. The pockets 14 may include a variety of depths within the metal tray 12 to accommodate a variety of medical instruments 16. For example, one metal tray 12 may include a plurality of pockets 14, each having a different depth. A shallower pocket 14 may be sized to house a small medical instrument 16 and a pocket 14 with a larger depth may house a larger medical instrument 16. In addition, one pocket 14 may include more than one depth. For example, a pocket 14 may include a constant depth in part of the pocket 14, with another depth or angled portion in a second part of the pocket 14. This may be used to accommodate medical instruments 16 that have a small part and a large part, such as a large medical instrument 16 having a small handle.

The cover 18 may be formed over the metal tray 12 by any known process, including a thermoforming or hydroforming process. The cover 18 may be formed independently from the metal tray 12 and then positioned over the metal tray 12. The cover 18 may have dimensions that substantially correspond to the dimensions of the metal tray 12. For example, as is shown in FIG. 1, the cover 18 may include a substantially planar portion surrounded by sides, which are positioned to match up with one or more sides of the metal tray 12. The metal tray 12 may not only function as a holder for one or more medical instruments 16, but may also include one or more supporting portions 13 on the metal tray 12, which support the sterilization apparatus 10. The supporting portions 13 may be located in any position on the metal tray 12. The cover 18 may be removably secured to the metal tray 12, which may include retaining the cover 18 in place with a fastening device 24. The fastening device 24 may include any type of device, design or structure that is capable of removably securing the cover 18 to the metal tray 12.

The sterilization apparatus 10 may also include a plurality of openings 22, which are holes or structures that allow a sterilization material to pass through the sterilization apparatus 10. The openings 22 may have any shape or design, such as circular, square or a combination there of, and may be located on any portion of the sterilization apparatus 10, including the cover 18, the metal tray 12 or any side of the cover 18 or metal tray 12. Furthermore, openings 22 may be located within the pockets 14, which may allow a sterilization material to exit the sterilization apparatus 10 after contacting a medical instrument 16. Different sized openings 22 may be used for different components of the sterilization apparatus 10.

The sterilization apparatus 10 is designed for use in the medical instrument sterilization industry using an auto clave or another sterilization device. The sterilization apparatus 10 may be used to house medical instruments 16 during a sterilization process, and to house already sterilized medical instruments 16 that are awaiting use in a medical procedure. Medical instruments 16 must be sterilized before use in a medical procedure to prevent infection or other illness from bacteria contamination. To minimize or prevent health hazards from bacteria contamination of a medical instrument 16, the sterilization apparatus 10 may include features to reduce the harboring of bacteria. This may include features to reduce cracks, crevices, perpendicular corners or similar bacteria-prone areas. For example, the portions of the metal tray 12 where the pockets 14 are formed may be chamfered or rounded to eliminate any bacteria-prone corners. With most molding processes, interior perpendicular corners are difficult to create due to the nature of removing a molded sheet of metal. Thus, many bacteria-prone corners may be eliminated through a molding or forming process that reduces cracks, crevices and perpendicular corners, that non-molding or non-forming processes are unable to achieve. However, additional bacteria-prone areas, such as the areas between the cover 18 and the metal tray 12, may be eliminated with a sealing structure, such as a knife-edge sealing structure.

Figure 2:
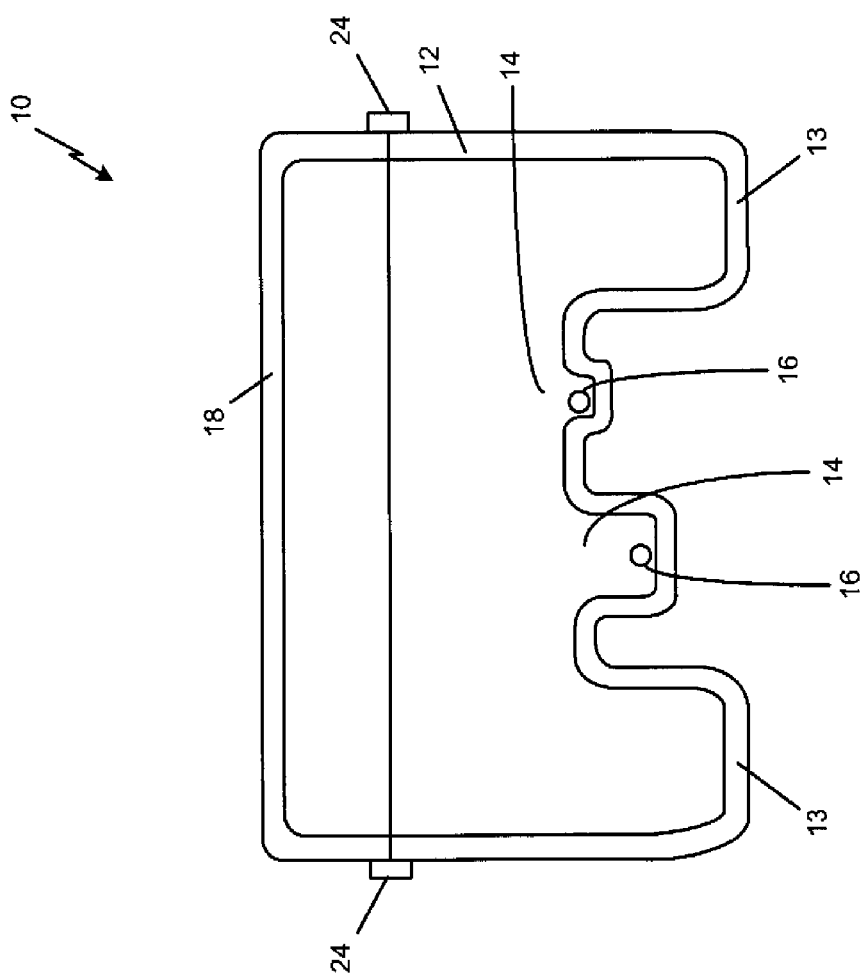
FIG. 2 is an illustration of a cross-sectional side view of a sterilization apparatus of FIG. 1, in accordance with the first exemplary embodiment of the present disclosure.

FIG. 2 is an illustration of a cross-sectional side view of a sterilization apparatus 10 of FIG. 1, in accordance with the first exemplary embodiment of the present disclosure. As can be seen in FIG. 2, the metal tray 12 includes a plurality of pockets 14 that may have different depths. The metal tray 12 may includes supporting structures 13, which function to support the sterilization tray 10. Although two supporting portions 13 are illustrated in FIG. 2, any number of supporting structures 13 may be used. Furthermore, the pockets 14 may have a secondary function and take the place of the supporting structures 13. Likewise, the supporting structures 13 may be sized to house a medical instrument 16.

Figure 3:
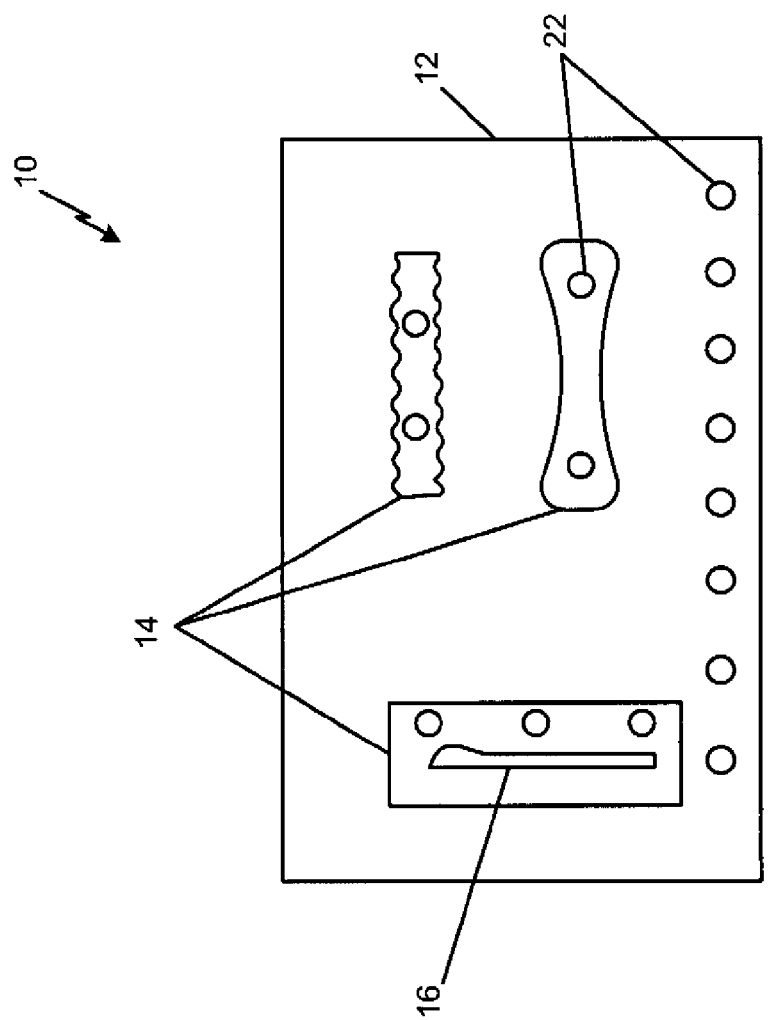
FIG. 3 is a top view of the metal tray of the sterilization apparatus of FIG. 1, in accordance with the first exemplary embodiment of the present disclosure.

FIG. 3 is a top view of the metal tray 12 of the sterilization apparatus 10 of FIG. 1, in accordance with the first exemplary embodiment of the present disclosure. The metal tray 12 may include a plurality of different sized and shaped pockets 14 for housing a plurality of medical instruments 16. A pocket 14 may be formed with a specific shape to conform to the shape of a particular medical instrument 16. The metal tray 12 may also include a plurality of openings 22, which may be located within a pocket 14 of the metal tray 12.

Figure 4:
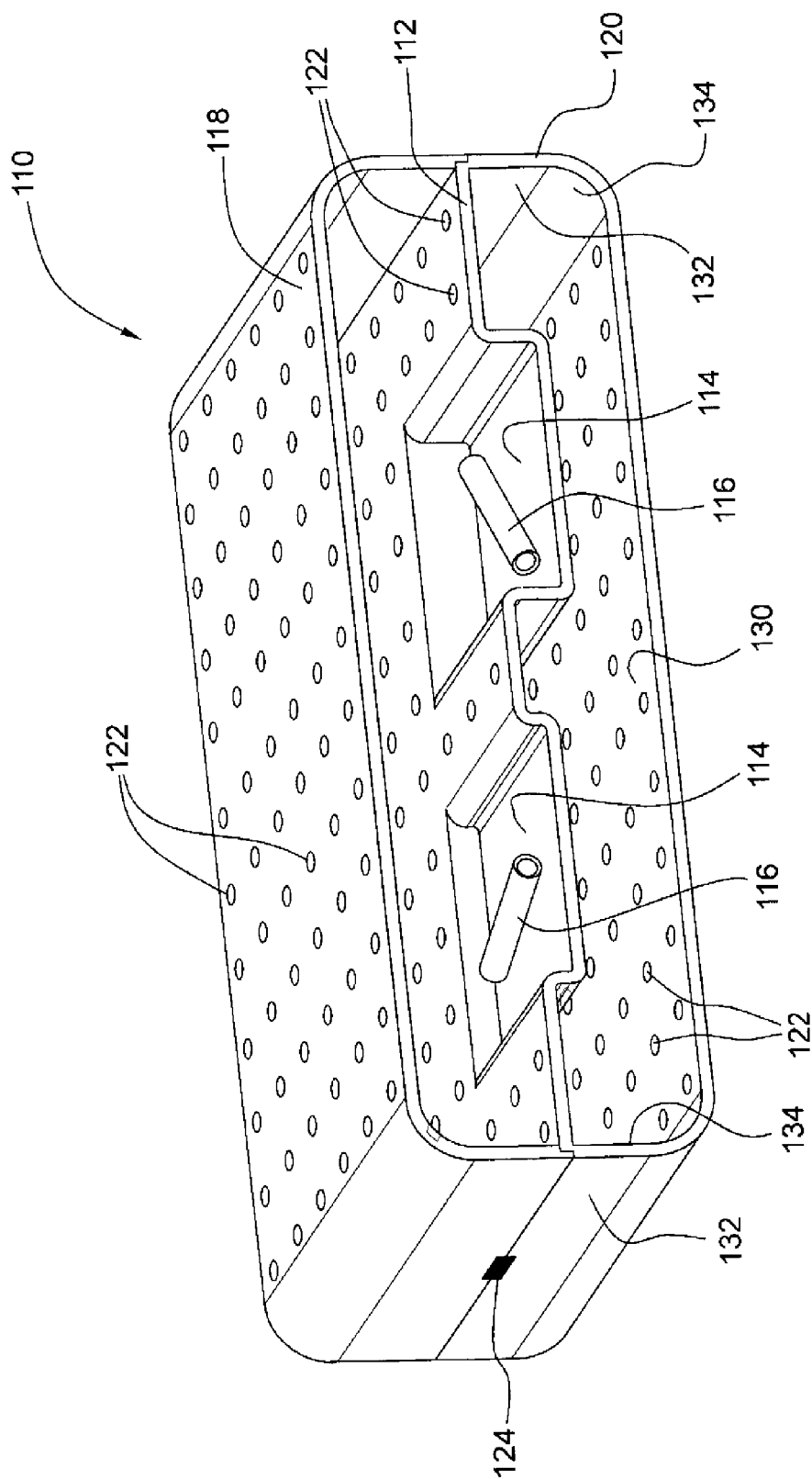
FIG. 4 is an illustration of a cross-sectional plan view of a sterilization apparatus, in accordance with a second exemplary embodiment of the present disclosure.

FIG. 4 is an illustration of a cross-sectional plan view of a sterilization apparatus 110, in accordance with a second exemplary embodiment of the present disclosure. The sterilization apparatus 110 of FIG. 4 may be substantially similar to the sterilization apparatus 10 of FIG. 1, but additionally includes a base structure 120 removably secured to the cover 118 or the metal tray 112. The base structure 120 may be formed from any of the molding or forming processes discussed in the first exemplary embodiment. The base structure 120 may be engaged with the cover 118, as is shown, wherein the metal tray 112 is formed to fit snugly between the cover 118 and the base structure 120. Additionally, the base structure 120 may be engaged with the metal tray 112, wherein the cover 118 is affixed to either the base structure 120 or the metal tray 112. The sterilization apparatus 110 may include one or more fasteners 124 to secure the base structure 120 to the cover 118, as is shown, or to the metal tray 112.

Any of the metal tray 112, the cover 118 and the base structure 120 may include a plurality of openings 122 formed within the metal tray 112, the cover 118 or the base structure 120, respectively. The plurality of openings 122 may permit a quantity of sterilization material to pass through the metal tray 112, the cover 118 or the base structure 120, respectively. Similar to the first exemplary embodiment, the sterilization apparatus 110 may include features to minimize bacteria harboring or bacteria contamination within the sterilization apparatus 110. For example, the base structure 120 may have a substantially planar interior portion 130 and a plurality of walls 132 rising in a substantially perpendicular direction from the interior portion 130. A plurality of corner portions 134 may be located between at least two of interior portion 130 and the plurality of walls 132, wherein the corner portions 134 have an arced surface. The arced surface may prevent bacteria from accumulating proximate to the corner portions 134 better than corner portions 134 without an arced surface, such as corner portions 134 that meet at a substantially 90° angle.

The sterilization apparatus 110 may further include variations and alternative designs, as is dependent on the use and requirements of the sterilization apparatus 110. For example, the sterilization apparatus 110 may include a plurality of metal trays 112 that can be stacked within the base structure 120. Sufficient space may be provided between the plurality of metal trays 112 to allow for a sterilization material to properly sterilize medical instruments 116 housed within the metal trays 112. Furthermore, the sterilization apparatus 110 may include identification labels or other indicia for properly identifying medical instruments 116 that are housed within the metal tray 112. Other features that may be included with the sterilization apparatus 110 include a metal tray 112 with fully chamfered or arced corners, thereby providing virtually no place for bacteria to become accumulated. Accordingly, the pockets 116 formed within the metal tray 112 may have sloped or angled sides to decrease or eliminate the number of substantially 90° angle corners within the sterilization apparatus 110. As one having ordinary skill in the art can see, a number of other features may be included with the sterilization apparatus 110, all of which are considered within the scope of the present disclosure.

Figure 5:
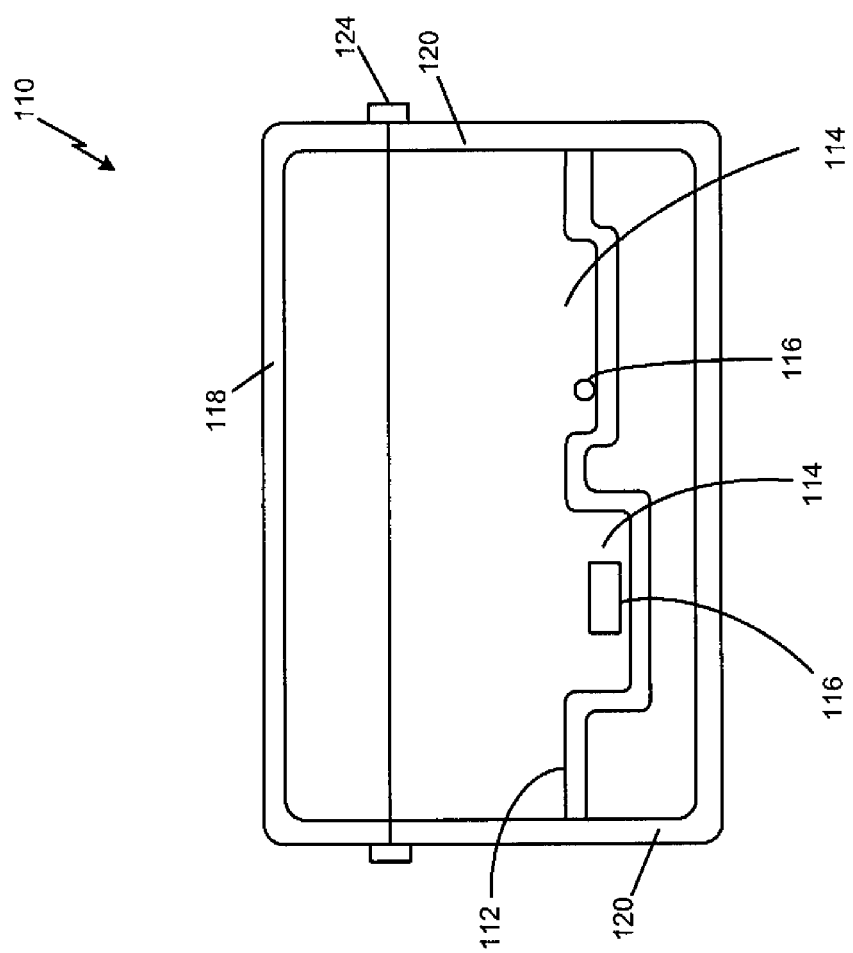
FIG. 5 is an illustration of a cross-sectional side view of a sterilization apparatus of FIG. 4, in accordance with the second exemplary embodiment of the present disclosure.

FIG. 5 is an illustration of a cross-sectional side view of a sterilization apparatus of FIG. 4, in accordance with the second exemplary embodiment of the present disclosure. As can be seen in FIG. 5, the metal tray 112 includes a plurality of pockets 114 that may have different depths. The metal tray 112 may be attached to the base structure 120 in any fashion, such as by lowering the metal tray 112 into the base structure 120 that has a shelf structure for supporting the metal tray 112. The metal tray 112 may also be formed to fit snugly between the cover 118 and the base structure 120. Additionally, the metal tray 112 may be removably or irremovably secured within the base structure 120, such as by welding or fastening the metal tray 112 to one or more of the plurality of walls 132 of the base 120.

Figure 6:
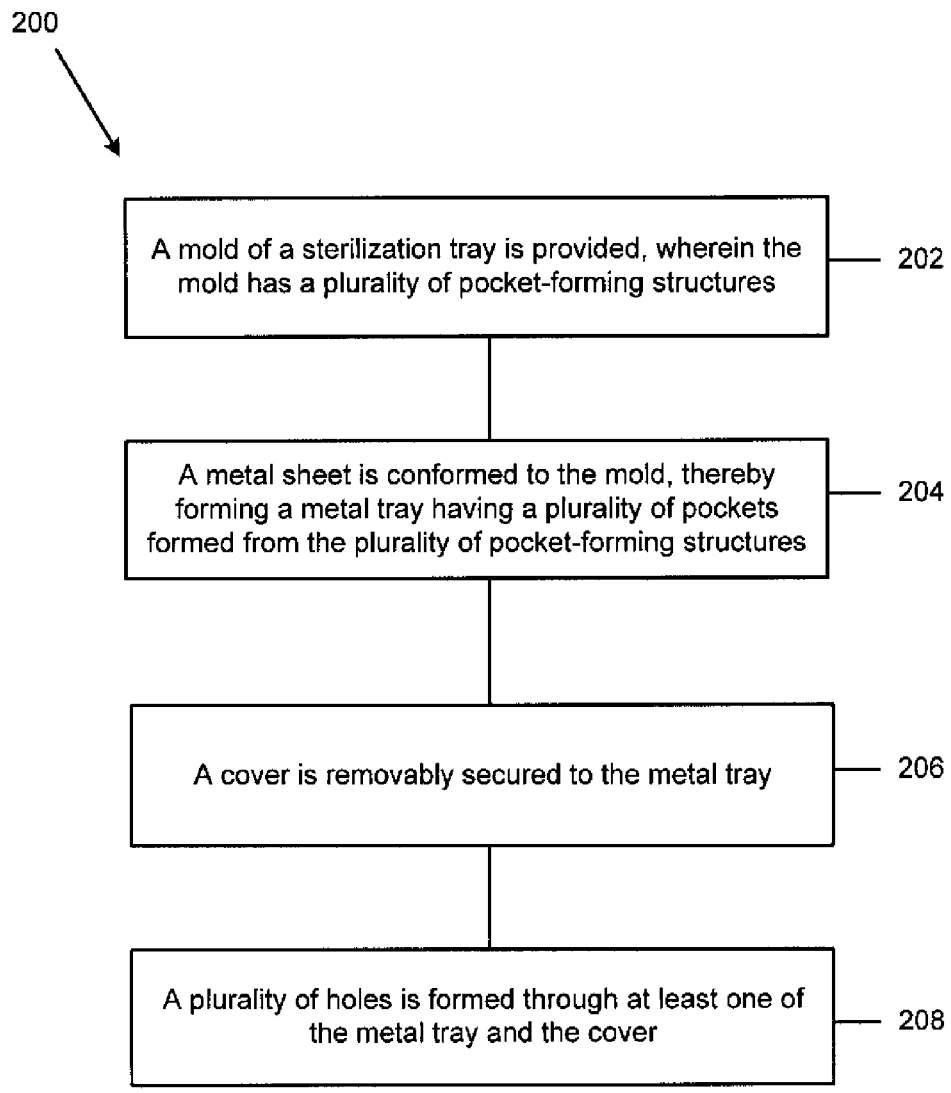
FIG. 6 is an illustration of a flowchart illustrating a method of forming the sterilization apparatus of FIG. 1, in accordance with the first exemplary embodiment of the present disclosure.

FIG. 6 is an illustration of a flowchart 200 illustrating a method of forming the sterilization apparatus of FIG. 1, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202 a mold of a sterilization tray is provided, wherein the mold has a plurality of pocket-forming structures. A metal sheet is conformed to the mold, thereby forming a metal tray having a plurality of pockets formed from the plurality of pocket-forming structures (block 204). A cover is removably secured to the metal tray (block 206). A plurality of holes is formed through at least one of the metal tray and the cover (block 208). The method of forming a sterilization apparatus may also include the steps of engaging a base with the cover and forming the metal tray to fit snugly between the cover and the base. Additionally, at least one of the plurality of pockets may be sized to provide a friction fit to a medical instrument, thereby retaining the medical instrument in a substantially stationary position within the metal tray.

The metal sheet may be made to conform by a process known as thermoforming. Metal sheets, such as aluminum sheets, are heated to a temperature fitting within a superplastic temperature window of the metal. At the superplastic temperature, the metal sheets are malleable, while maintaining sufficient integrity to avoid uneven thinning. The heated metal sheet is set to a mold and the metal sheet conforms to the mold over a period of about 10 minutes, for example. Using the thermoforming process, a metal sterilization tray may be formed from a unitary sheet of metal that retains and segregates medical instruments without the need for additional brackets, dividers and the like. The number of crevices can be reduced or eliminated by avoiding attachment elements. Also, if aluminum or another lightweight metal is selected, the metal tray can be made lighter than a comparable plastic tray due to the weight of the aluminum and the avoidance of additional parts.

The metal sheet may be made to conform by a process known as hydroforming. Metal sheets, such as aluminum sheets, are pressed against a mold by an expanding bladder that increases pressure on the metal sheets as the bladder expands. Using the hydroforming process, a metal sterilization tray may be formed from a unitary sheet of metal that retains and segregates medical instruments without the need for additional brackets, dividers and the like. The number of crevices can be reduced or eliminated by avoiding attachment elements. Also, if aluminum or another lightweight metal is selected, the metal tray can be made lighter than a comparable plastic tray due to the weight of the aluminum and the avoidance of additional parts.

Figure 7:
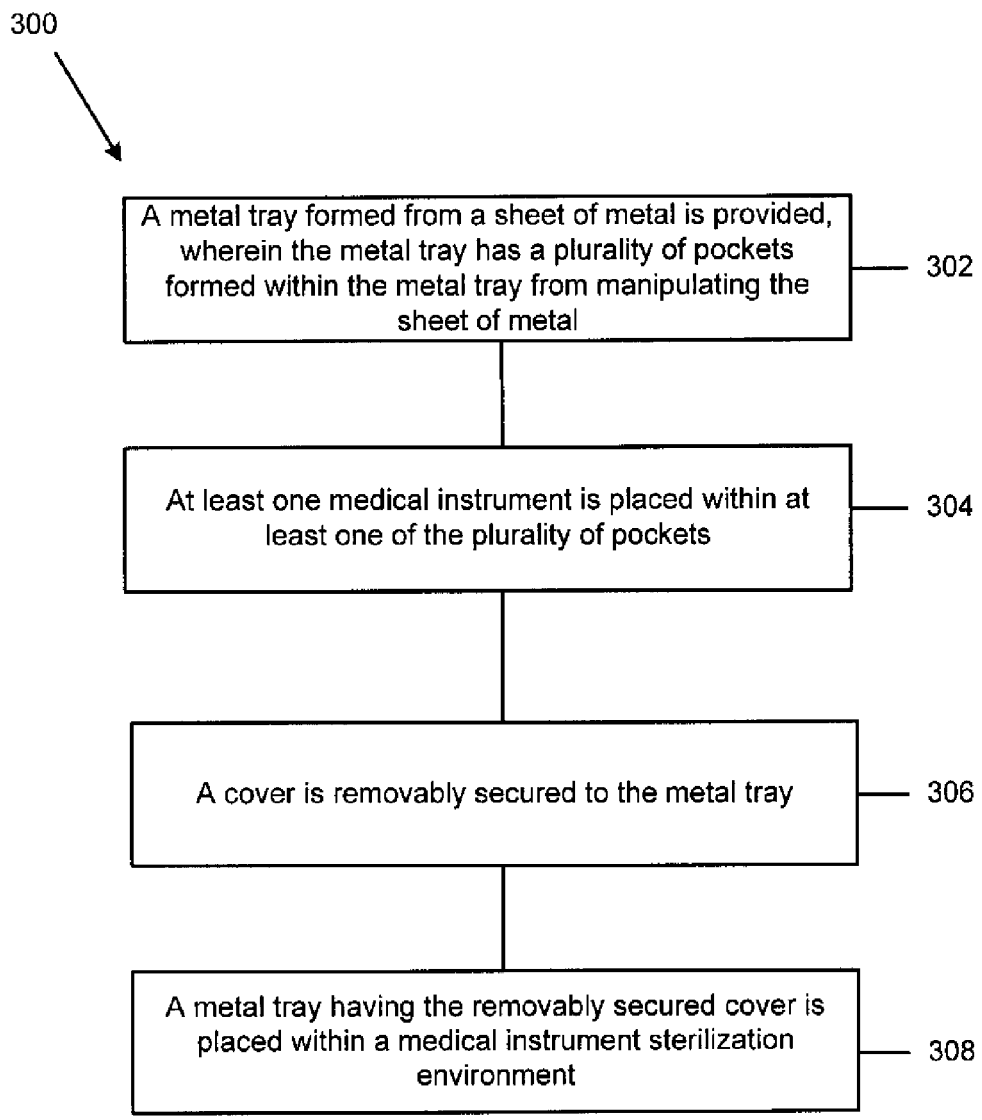
FIG. 7 is an illustration of a flowchart illustrating a method of sterilizing a medical instrument, in accordance with a third exemplary embodiment of the present disclosure.

FIG. 7 is an illustration of a flowchart 300 illustrating a method of sterilizing a medical instrument, in accordance with a third exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302, a metal tray formed from a sheet of metal is provided, wherein the metal tray has a plurality of pockets formed within the metal tray from manipulating the sheet of metal. At least one medical instrument is placed within at least one of the plurality of pockets (block 304). A cover is removably secured to the metal tray (block 306). The metal tray having the removably secured cover is placed within a medical instrument sterilization environment (block 308). Additional steps may also be included to enhance the sterilization process, such as providing a plurality of openings within the metal tray, the cover or a base, thereby allowing a sterilization material to contact a medical instrument within the metal tray.

It should be emphasized that the above-described embodiments of the present disclosure, particularly, any "preferred" embodiments, are merely possible examples of implementations, merely set forth for a clear understanding of the principles of the disclosed system and method. Many variations and modifications may be made to the above-described embodiments of the disclosure without departing substantially from the spirit and principles of the disclosure. All such modifications and variations are intended to be included herein within the scope of this disclosure and protected by the following claims.

What is claimed is:

1. A sterilization apparatus, comprising:
   a metal tray formed from a unitary sheet of metal:
   a plurality of pockets formed in the metal tray, wherein the plurality of pockets is formed from manipulating the unitary sheet of metal;
   a cover formed over the metal tray; and a base removably fastened to the cover, wherein the metal tray is formed to fit snugly between the cover and the base when fastened together.

2. The sterilization apparatus of claim 1, further comprising a plurality of openings formed within the base, wherein the plurality of openings permit a quantity of sterilization material to pass through the base.

3. The sterilization apparatus of claim 1, wherein the base has a substantially planar interior portion, a plurality of walls rising in a substantially perpendicular direction from the interior portion and a plurality of corner portions connected between at least two of interior portion and the plurality of walls, wherein the corner portions have arced surfaces to minimize an amount of bacteria capable of being harbored proximate to the corner portions.

4. A sterilization apparatus, comprising:
   a metal tray formed from a unitary sheet of metal;
   a plurality of pockets formed in the metal tray, wherein the plurality of pockets is formed from manipulating the unitary sheet of metal;
   a cover formed over the metal tray; and
   a plurality of openings formed within one of the metal tray and the cover, wherein the plurality of openings permit a quantity of sterilization material to pass through at least one of the metal tray and the cover.

5. A sterilization apparatus, comprising:
   a metal tray formed from a unitary sheet of metal;
   a plurality of pockets formed in the metal tray, wherein the plurality of pockets is formed from manipulating the unitary sheet of metal;
   a cover formed over the metal tray; and
   wherein a first pocket of the plurality of pockets formed in the metal tray has a first depth and a second pocket of the plurality of pockets has a second depth, wherein the first pocket is different from the second pocket and wherein the first depth is different from the second depth.

6. A sterilization apparatus, comprising:
a metal tray formed from a unitary sheet of metal;
a plurality of pockets formed in the metal tray, wherein the plurality of pockets is formed from manipulating the unitary sheet of metal;
a cover formed over the metal tray;
wherein the cover is removably fastened directly to the metal tray, and
wherein the cover is removably fastened directly to the metal tray with at least one fastener engaged directly between the cover and the metal tray.

* * * * *